United States Patent [19]
Reiffenrath et al.

[11] Patent Number: 5,213,710
[45] Date of Patent: May 25, 1993

[54] BENZENE DERIVATIVES AND A LIQUID-CRYSTALLINE MEDIUM

[75] Inventors: Volker Reiffenrath, Rossdorf; Reinhard Hittich, Modautal; Herbert Plach, Darmstadt, all of Fed. Rep. of Germany

[73] Assignee: Merck Patent Gesellschaft Mit Beschrankter Haftung, Darmstadt, Fed. Rep. of Germany

[21] Appl. No.: 765,775

[22] Filed: Sep. 26, 1991

[30] Foreign Application Priority Data

Sep. 26, 1990 [DE] Fed. Rep. of Germany ....... 4030392
Feb. 28, 1991 [DE] Fed. Rep. of Germany ....... 4106344
Apr. 11, 1991 [DE] Fed. Rep. of Germany ....... 4111765

[51] Int. Cl.$^5$ .................. C09K 19/30; C09K 19/12; C07C 22/00; C07C 19/08
[52] U.S. Cl. .................. 252/299.63; 252/299.66; 570/128; 570/144
[58] Field of Search ............. 252/299.63, 299.66; 570/128, 144

[56] References Cited

U.S. PATENT DOCUMENTS

| | | | |
|---|---|---|---|
| 3,923,305 | 12/1966 | Haszeldine | 570/129 X |
| 4,256,656 | 3/1981 | Beguin et al. | 558/416 X |
| 4,545,921 | 10/1985 | Dubois et al. | 252/299.62 |
| 4,551,264 | 11/1985 | Eidenschink et al. | 252/299.62 |
| 4,614,608 | 9/1986 | LeBarny et al. | 252/299.64 |
| 5,032,313 | 7/1991 | Goto et al. | 252/299.63 |

FOREIGN PATENT DOCUMENTS

| | | |
|---|---|---|
| 3902328 | 8/1990 | Fed. Rep. of Germany . |
| 0018326 | 2/1983 | Japan . |
| 8909203 | 10/1989 | World Int. Prop. O. . |

OTHER PUBLICATIONS

Toyne, K. J., *Thermotropic Liquid Crystals*, G. W. Gray (Ed.), vol. 22, Chapter 2.7, pp. 47-63.

*Primary Examiner*—Robert L. Stoll
*Assistant Examiner*—C. Harris
*Attorney, Agent, or Firm*—Millen, White, Zelano & Branigan

[57] ABSTRACT

The invention relates to novel benzene derivatives of the formula I

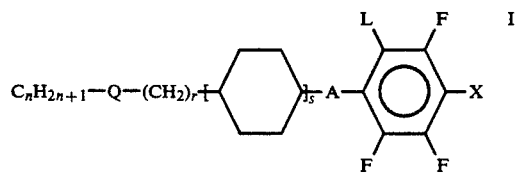

in which
n is 0, 1, 2, 3, 4, 5, 6 or 7,
Q is —O—, —CH=CH— or a single bond,
r is 0, 1, 2, 3, 4 or 5,
s is 0, 1 or 2,
X is F, Cl, OCHF$_2$ or CF$_3$,
L is H or F, and
A is

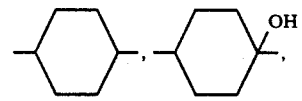

Z, Z-Ar, Ar-Z, Z-Cyc in which Z is a single bond, —(CH$_2$)$_2$— or —(CH$_2$)$_4$—, Ar is 1,4-phenylene or biphenyl-4,4'-diyl and Cyc is trans-1,4-cyclohexylene.

17 Claims, No Drawings

BENZENE DERIVATIVES AND A LIQUID-CRYSTALLINE MEDIUM

SUMMARY OF THE INVENTION

The invention relates to novel benzene derivatives of the formula I

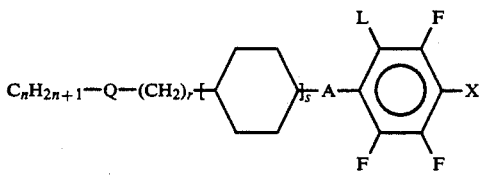

in which
n is 0, 1, 2, 3, 4, 5, 6 or 7,
Q is —O—, —CH=CH— or a single bond,
r is 0, 1, 2, 3, 4 or 5,
s is 0, 1 or 2,
X is F, Cl, $OCHF_2$ or $CF_3$,
L is H or F, and
A is

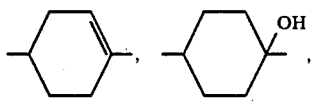

Z, Z-Ar, Ar-Z, Z-Cyc in which Z is a single bond, —$(CH_2)_2$— or —$(CH_2)_4$—, Ar is 1,4-phenylene or biphenyl-4,4'-diyl and Cyc is trans-1,4-cyclohexylene.

EP-A 0 184 012 discloses liquid crystals of the formulae below:

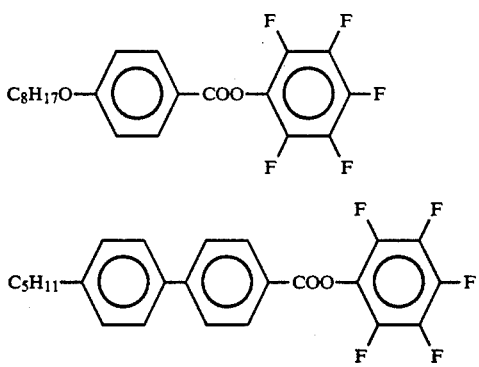

However, the compounds described therein are esters which do not meet the high stability requirements for modern display applications.

Like similar compounds, for example those disclosed in DE-A 32 11 601, the compounds of the formula I can be used as components of liquid-crystalline media, in particular for displays based on the principle of the twisted cell.

All the substances employed hitherto for this purpose have certain disadvantages, for example excessively high melting points, excessively low clearing points, inadequate stability to the action of heat, light or electrical fields, inadequate electrical resistance, excessive temperature dependence of the threshold voltage and unfavorable elastic and/or dielectric properties.

In particular in displays of the supertwist type (STN) having twist angles of significantly greater than 220° or in displays having an active matrix, the materials employed hitherto have disadvantages.

The invention had the object of finding novel liquid-crystalline compounds which are suitable as components of liquid-crystalline media, in particular for nematic media having positive dielectric anisotropy, and which do not have the disadvantages of the known compounds, or only do so to a lesser extent. This object has been achieved by the provision of the novel compounds of the formula I.

It has been found that the compounds of the formula I are eminently suitable as components of liquid-crystalline media. They can be used, in particular, to obtain liquid-crystalline media having broad nematic ranges, excellent nematogeneity down to low temperatures, excellent chemical stability, excellent elastic properties, low temperature dependence of the threshold voltage and/or low optical anisotropy. In addition, the novel compounds have good solubility for other components of media of this type and high positive dielectric anisotropy at the same time as favorable viscosity.

The compounds of the formula I make it possible to produce STN displays with a very steep electrooptical characteristic line and displays having an active matrix and excellent long-term stability. The threshold voltages can be significantly reduced in displays of both types by a suitable choice of r and n.

In the pure state, compounds of the formula I are colorless and form liquid-crystalline mesophases in a temperature range which is favorable for electrooptical use.

The invention thus relates to the compounds of the formula I and to the use of the compounds of the formula I as components of liquid-crystalline media, to liquid-crystalline media containing at least one compound of the formula I, and to electrooptical displays which contain media of this type.

Above and below, r, s, n, A, L and Q are as defined above, unless expressly stated otherwise.

In the compounds of the formula I, the alkyl groups $C_nH_{2n+1}$ are preferably straight-chain. Accordingly, $C_nH_{2n+1}$ is preferably methyl, ethyl, n-propyl, n-butyl, n-pentyl, n-hexyl or n-heptyl. n is preferably 1, 2, 3, 4 or 5, particularly preferably 1 if Q is —O—. If Q is —CH=CH—, n is preferably 0. r is preferably 3 or 4. r is furthermore preferably 5. If Q is a single bond, r is preferably 0.

Compounds of the formula I containing branched alkyl groups may occasionally be of importance due to better solubility in the customary liquid-crystalline base materials, but in particular as chiral dopes if they are optically active. Branched groups of this type generally contain not more than one chain branch. Preferred branched alkyl radicals are isopropyl, 2-butyl (=1-methylpropyl), isobutyl (=2-methylpropyl), 2-methylbutyl, isopentyl, (=3-methylbutyl), 2-methylpentyl, 3-methylpentyl and 2-heptyl (=1-methylhexyl).

Particular preference is given to:
the compounds of the formula Ia,

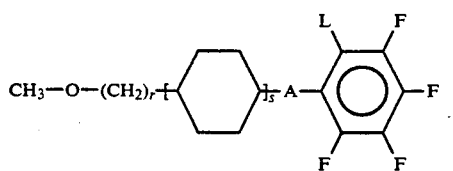

Ia in which r is 2, 3, 4 or 5, s is 1 or 2, and A and L are as defined in Formula I, the compounds of the formula Ib

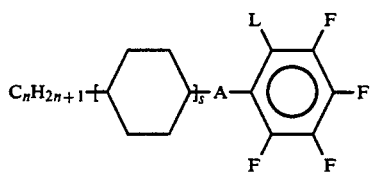

Ib in which n is 1 to 7, s is 1 or 2, and A and L are as defined in Formula I.

Here, s is preferably 2, and A=Z (Z is preferably a single bond or —(CH$_2$)$_2$—) or s=1 and A=Ar.

Ar is generally preferably 1,4-phenylene. A is preferably 1,4-phenylene or a single bond.

Particular preference is likewise given to the compounds of the formula Ic

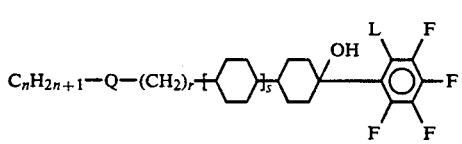

Ic in which n is 1 to 7, s is 0, 1 or 2, and Q, r and L are as defined in Formula I, the compounds of the formula Id

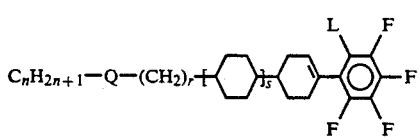

Id in which n is 1 to 7, s is 0, 1 or 2, and Q, r and L are as defined in Formula I, the compounds of the formula Ie

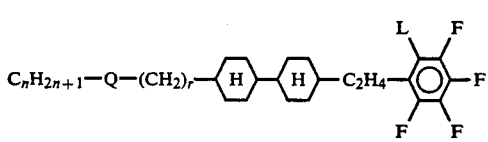

Ie in which n is 1 to 7, and Q, r and L are as defined in Formula I, the compounds of the formula If

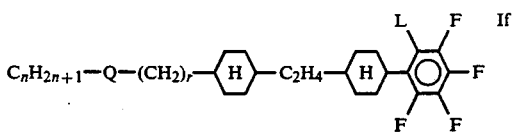

If in which n is 1 to 7, and Q, r and L are as defined in Formula I.

Preference is furthermore given to the compounds

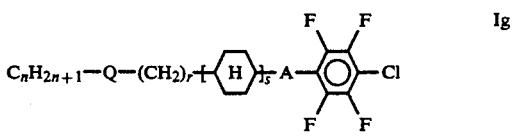

Ig

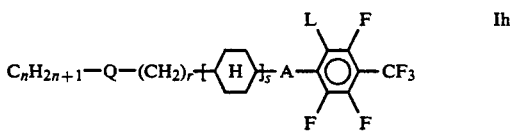

Ih

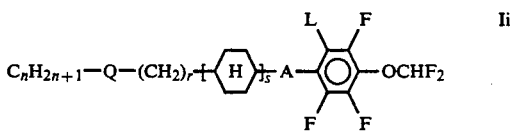

Ii in which n is 1 to 7, s is 0, 1 or 2, and Q, r and L are as defined in Formula I, In addition, the compounds of the formula I are prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and are suitable for said reactions. Use may also be made here of variants which are known per se, but are not described here in greater detail.

If desired, the starting materials can also be formed in situ by not isolating them from the reaction mixture, but instead immediately converting them further into the compounds of the formula I.

The precursors which are suitable for the synthesis of the compounds according to the invention are obtainable, for example, in accordance with the following synthesis scheme:

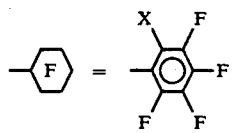

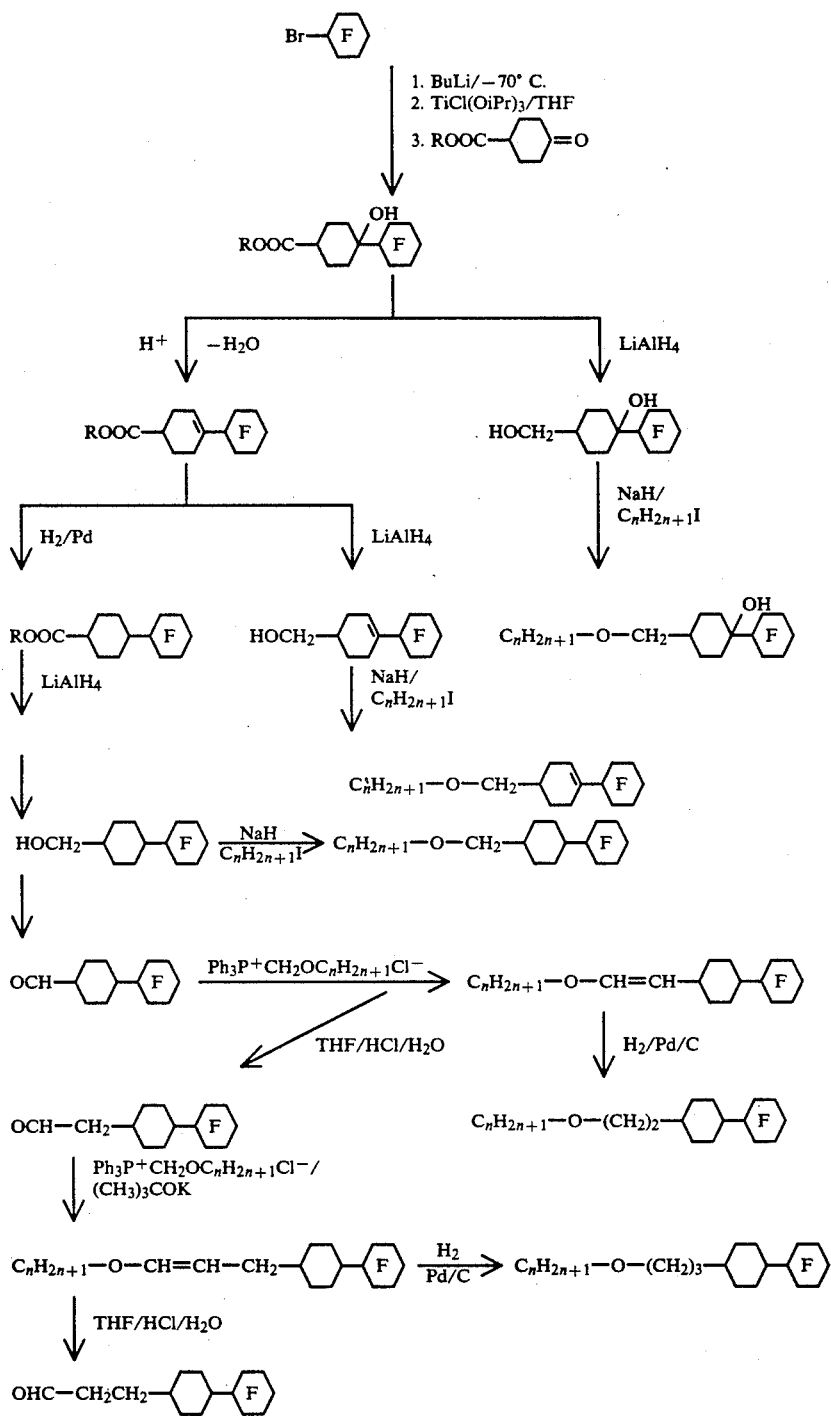

Appropriate repetition of this reaction sequence gives the compounds where r is 4 or 5.

The corresponding aldehydes in which s is 1 and A is 1,4-phenylene can be prepared analogously to the above synthesis scheme, with the bromobenzene derivative being replaced by a compound

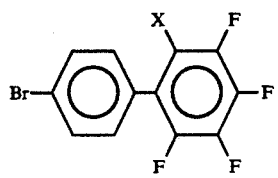

which can be prepared by transition metal-catalysed coupling reactions (E. Poetsch, Kontakte (Darmstadt) 1988, p. 15).

The Grignard compound obtained from the corresponding bromobenzene derivative is reacted with chlorotrialkyl orthotitanate or -zirconate by the method of WO 87/05599 to give the tertiary cyclohexanol. Elimination of water, hydrogenation of the double bond and isomerisation give, by customary methods, the trans-cyclohexanecarboxylic acid ester. From the latter are obtained, by customary standard methods, the aldehydes which are suitable for the compounds according to the invention, which are obtainable from the latter by the Wittig synthesis with subsequent hydrogenation of the double bond.

Some of the bromobenzene derivatives used as starting materials are known and some can be prepared without difficulties by standard methods of organic chemistry from compounds which are known from the literature.

The homologization indicated in the above reaction scheme can also be carried out by other standard methods known to a person skilled in the art.

The compounds according to the invention where s=2 are synthesized by the following synthesis scheme:

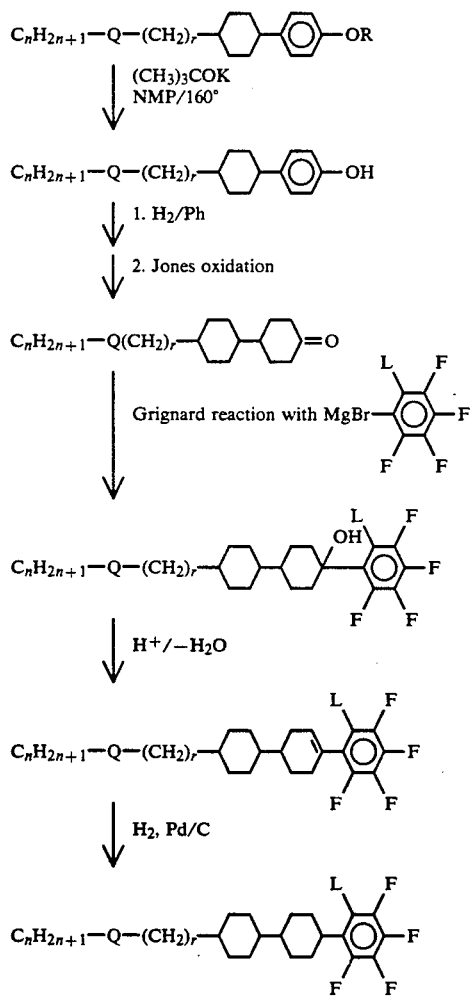

A further possibility for the preparation of the preferred compounds where r=3 and n=1 is indicated below:

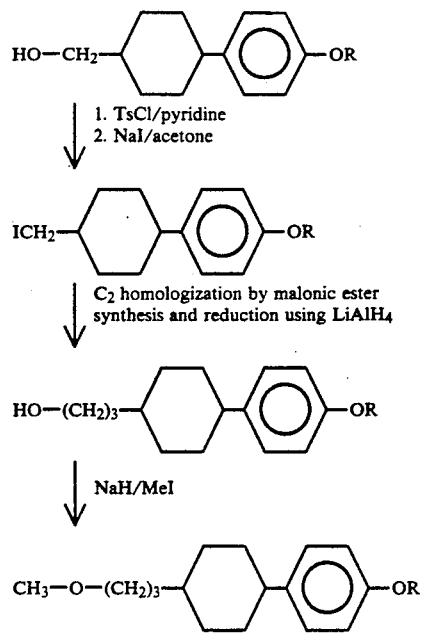

The synthesis of some particularly preferred compounds is given in the schemes below:

Scheme 1

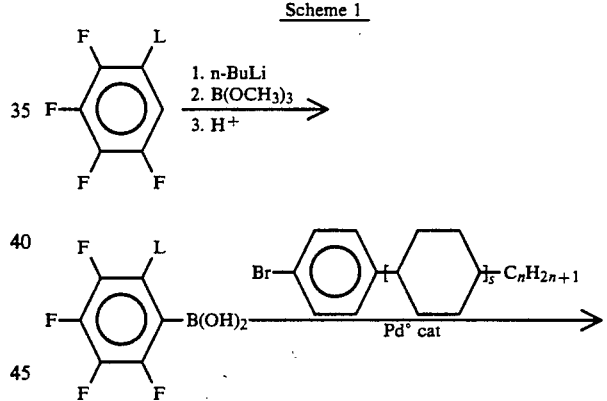

Scheme 2

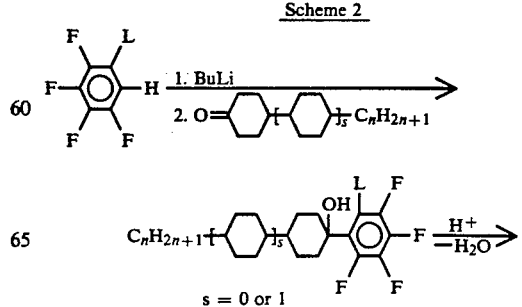

s = 0 or 1

Scheme 2

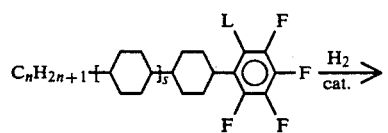
$\xrightarrow{\text{H}_2 \text{ cat.}}$

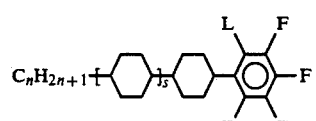

Scheme 3

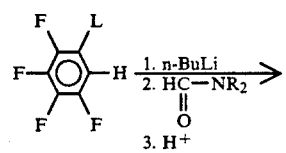
$\xrightarrow[\substack{2.\ \text{HC}-\text{NR}_2 \\ \quad\ \ \parallel \\ \quad\ \ \text{O} \\ 3.\ \text{H}^+}]{1.\ n\text{-BuLi}}$

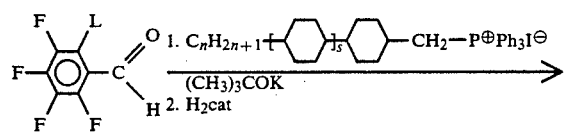

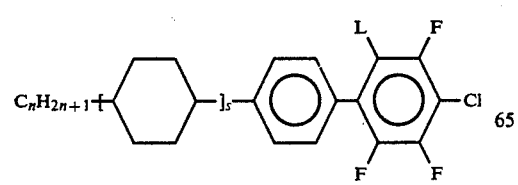

s = 0 or 1

Scheme 4

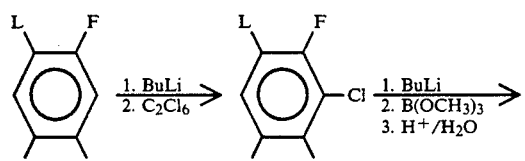

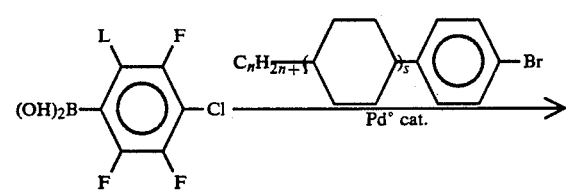

Scheme 5

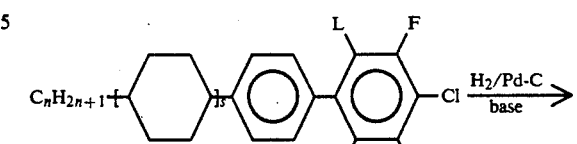
$\xrightarrow[\text{base}]{\text{H}_2/\text{Pd-C}}$

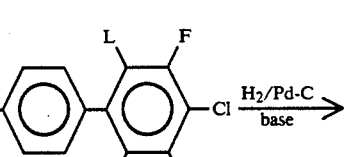
$\xrightarrow{\substack{1.\ \text{BuLi} \\ 2.\ \text{I}_2}}$

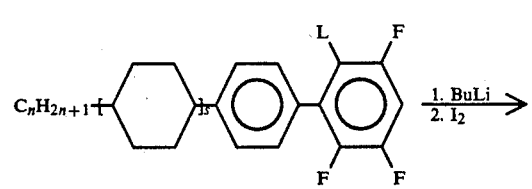
$\xrightarrow[\Delta]{\text{CF}_3\text{COONa}/\text{CuI}}$

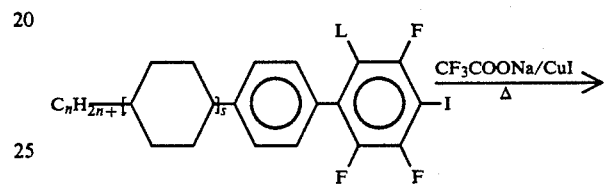

Scheme 6

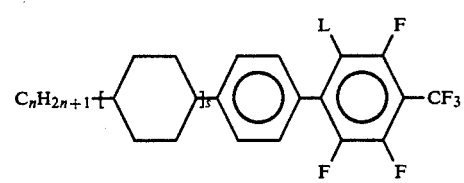
$\xrightarrow[\substack{2.\ C_n H_{2n+1}\text{—}\bigcirc\text{—}\bigcirc=\text{O}}]{1.\ \text{BuLi}}$

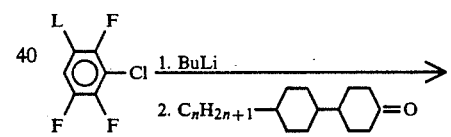
$\xrightarrow[-\text{H}_2\text{O}]{+\text{H}^+}$

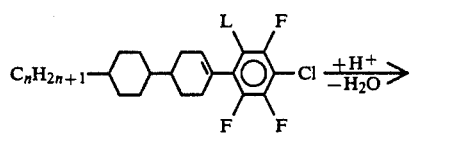
$\xrightarrow{\substack{1.\ \text{H}_2/\text{Ra—Ni}/\text{H}^+ \\ 2.\ \text{H}_2/\text{Pd—C}/\text{base}}}$

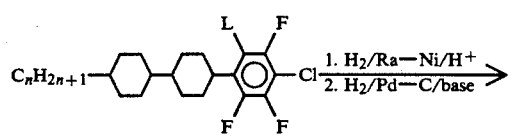
$\xrightarrow{\substack{1.\ \text{BuLi} \\ 2.\ \text{B}(\text{OCH}_3)_3 \\ 3.\ \text{H}_2\text{O}_2/\text{H}^+ \\ 4.\ \text{ClCHF}_2/\text{base}}}$

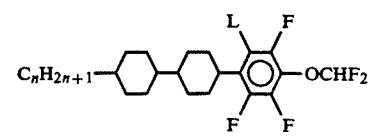

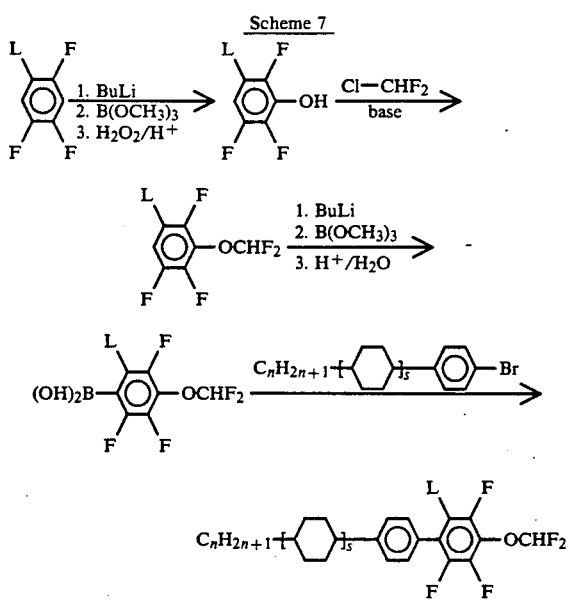

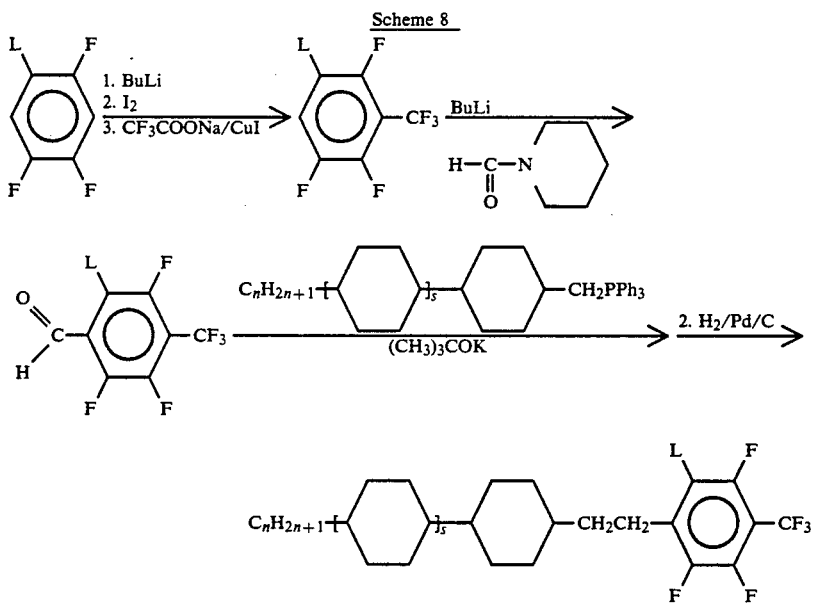

clohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl- 2-cyclohexylethanes, 1-cyclohexyl-2-(4-phenylcyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterised by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simul- The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcytaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, F, Cl or —NCS; in this case, R has the meaning given for the compounds of the sub-formulae 1a to 5a and is preferably alkyl or alkenyl. R" is preferably selected from the group comprising —F, Cl, CF$_3$ and —OCF$_3$. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:
Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the present application and in the examples below, the structures of the liquid-crystal compounds are indicated by means of acronyms, with the transformation into chemical formulae taking place in accordance with Tables A and B below. All the radicals $C_nH_{2n+1}$ and $C_mH_{2m+1}$ are straight-chain alkyl radicals containing n and m carbon atoms respectively. The coding in Table B is self-evident. In Table A, only the acronym of the parent structure is indicated. In individual cases, the acronym for the parent structure is followed, separated by a dash, by the code for the substituents $R^1$, $R^2$, $L^1$, $L^2$ and $L^3$;

| Code for $R^1$, $R^2$, $L^1$, $L^2$, $L^3$ | $R^1$ | $R^2$ | $L^1$ | $L^2$ | $L^3$ |
| --- | --- | --- | --- | --- | --- |
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| nT | $C_nH_{2n+1}$ | CN | H | H | H |
| nN.F | $C_nH_{2n+1}$ | CN | H | F | H |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | F | H |
| nOmFF | $C_nH_{2n+1}$ | $OC_mH_{2m+1}$ | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_2$ | $C_2H_{2n+1}$ | OCHF$_2$ | H | H | H |
| nS | $C_2H_{2n+1}$ | NCS | H | H | H |
| rVsN | $C_rH_{2r+1}$—CH=CH—$C_sH_{2s}$— | CN | H | H | H |
| rEsN | $C_rH_{2r+1}$—O—$C_sH_{2s}$— | CN | H | H | H |
| nNF | $C_nH_{2n+1}$ | CN | F | H | H |
| nAm | $C_nH_{2n+1}$ | $COOC_mH_{2m+1}$ | H | H | H |
| nF.F.F | $C_nH_{2n+1}$ | F | H | F | F |
| nF.F.F.F | $C_nH_{2n+1}$ | F | F | F | F |

TABLE A

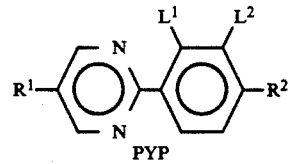

PYP

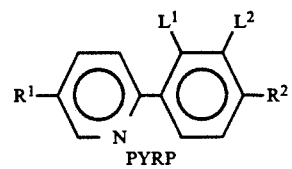

PYRP

TABLE A-continued

BCH, CBC, CCH, CCP, CP, CPTP, CEPTP, D, ECCP

CECP, EPCH, HP, ME, PCH, PDX, PTP, BECH, EBCH

TABLE A-continued

CPC: R¹—[H]—[⌬]—[H]—R²

CUP-nX: $C_nH_{2n+1}$—[H]—[⌬-2,6-F]—[⌬]—X

CUP-nX.F: $C_nH_{2n+1}$—[H]—[H-2-F]—[⌬-3-F]—X

TABLE B

T15: $C_5H_{11}$—[⌬]—[⌬]—[⌬]—CN

K3n: $C_nH_{2n+1}$—[⌬]—[⌬]—CN

M3n: $C_nH_{2n+1}$—O—[⌬]—[⌬]—CN

BCH-n.Fm: $C_nH_{2n+1}$—[H]—[⌬-F]—[⌬]—$C_mH_{2m+1}$

Inm: $C_nH_{2n+1}$—[H]—$C_2H_4$—[⌬-F]—[⌬]—$C_mH_{2m+1}$

C-nm: $C_nH_{2n+1}$—[H]—[H]—OOC—$C_mH_{2m+1}$

C15: $C_2H_5$—CH(CH₃)—CH₂—O—[⌬]—[⌬]—CN

CB15: $C_2H_5$—CH(CH₃)—CH₂—[⌬]—[⌬]—CN

CBC-nmF: $C_nH_{2n+1}$—[H]—[⌬]—[⌬-F]—[H]—$C_mH_{2m+1}$

TABLE B-continued

CCN-nm: $C_nH_{2n+1}$—[H]—[H-CN,$C_mH_{2m+1}$]

CCPC-nm: $C_nH_{2n+1}$—[H]—[H]—COO—[⌬]—[H]—$C_mH_{2m+1}$

CH-nm: $C_nH_{2n+1}$—[H]—[H]—COO—[H]—$C_mH_{2m+1}$

HD-nm: $C_nH_{2n+1}$—[H]—[⌬]—OOC—[H]—$C_mH_{2m+1}$

HH-nm: $C_nH_{2n+1}$—[H]—[⌬]—COO—[H]—$C_mH_{2m+1}$

NCB-nm: $C_nH_{2n+1}$—[⌬]—[⌬]—[H-CN,$C_mH_{2m+1}$]

OS-nm: $C_nH_{2n+1}$—[H]—COO—[H]—$C_mH_{2m+1}$

CHE: $C_2H_5$—[H]—COO—[⌬]—[⌬]—CN

ECBC-nm: $C_nH_{2n+1}$—[H]—$C_2H_4$—[⌬]—[⌬]—[H]—$C_mH_{2m+1}$

ECCH-nm: $C_nH_{2n+1}$—[H]—$C_2H_4$—[H]—$C_mH_{2m+1}$

CCH-n1EM: $C_nH_{2n+1}$—[H]—[H]—$CH_2O$—$C_mH_{2m+1}$

T-nFn: $C_nH_{2n+1}$—[⌬]—[⌬-F]—[⌬]—CN

ECCH-nm: $C_nH_{2n+1}$—[H]—$C_2H_4$—[H]—$C_mH_{2m+1}$

EXAMPLES

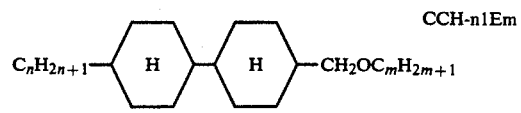

CCH-n1Em: $C_nH_{2n+1}$—[H]—[H]—$CH_2OC_mH_{2m+1}$

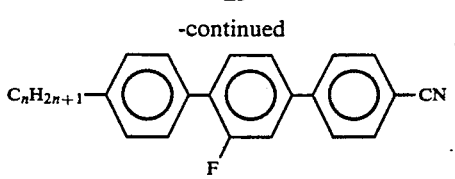

T-nFN

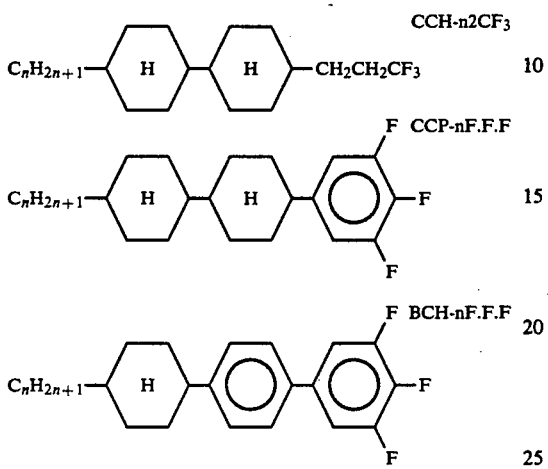

CCH-n2CF₃

CCP-nF.F.F

BCH-nF.F.F

The examples below are intended to illustrate the invention without representing a limitation. m.p.=melting point, c.p.=clearing point. Above and below, percentages are percent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following means: C: crystalline-solid state, S: smectic phase (the index characterizes the phase type), N: nematic state, Ch: cholesteric phase, I: isotropic phase. The number between two symbols indicates the transition temperature in degrees Celsius.

| DAST | diethylaminosulfur trifluoride |
|---|---|
| DCC | dicyclohexylcarbodiimide |
| DDQ | dichlorodicyanobenzoquinone |
| DIBALH | diisobutylaluminiun hydride |
| DMSO | dimethyl sulfoxide |
| POT | potassium tert.-butoxide |
| THF | tetrahydrofuran |
| pTSOH | p-toluenesulfonic acid |

EXAMPLE 1

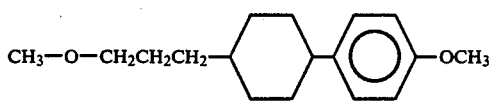

60 ml of THF are added under an N₂ atmosphere to 100 mmol of NaH in the form of an oil dispersion. The mixture is stirred vigorously and heated to 45° C.–50° C. 120 mmol of methyl iodide are then added, and 80 mmol of trans-4-(p-methoxyphenyl)cyclohexylpropyl alcohol [prepared as described above by malonic ester synthesis and reduction using LiAlH₄] in 20 ml of THF are subsequently added dropwise over the course of 30 minutes. The mixture is subsequently stirred for a further 30 minutes at the same temperature, and the reaction mixture is then cooled and carefully hydrolyzed using aqueous THF. When the vigorous evolution of H₂ is complete, the mixture is subjected to customary work-up, giving trans-4-(4-oxapentyl)-(p-methoxyphenyl)cyclohexane, C 19 N (15.1) I.

EXAMPLE 2

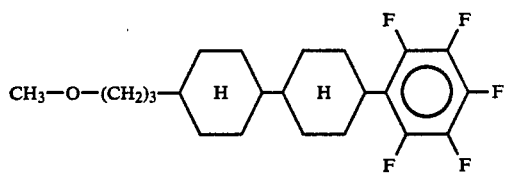

0.1 mol of magnesium and 0.1 mol of bromopentafluorobenzene are reacted in THF under an N₂ atmosphere to give the corresponding Grignard compound, to which 0.1 mol of 4-(trans-4-(4-oxapentyl)cyclohexyl)cyclohexanone [prepared from the compound of Example 1 by catalytic hydrogenation and Jones oxidation] is added, and the reaction mixture is stirred at the boiling point for 1 hour. The mixture is then subjected to customary work-up, and the reaction product is dehydrated on a water separator by boiling with p-toluenesulfonic acid in toluene. The reaction product is subsequently hydrogenated on a Pd/C catalyst. After customary basic isomerization, the isomers are separated by chromatography or crystallization, giving trans,trans-4-(4-oxapentyl)-4'-(p-pentafluorophenyl)-bicyclohexyl.

The following compounds of the formula

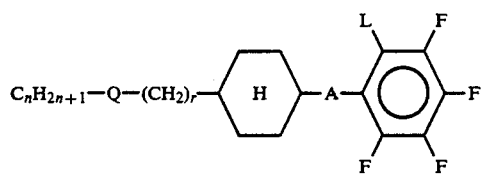

are obtained analogously or by dehydration of the cyclohexene intermediate using chloranil:

| $C_nH_{2n+1}$-Q-$(CH_2)_r$ | A | L | |
|---|---|---|---|
| $C_2H_5$ | 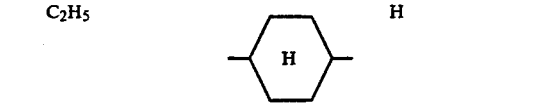 | H | |
| $C_2H_5$ |  | F | |
| n-$C_3H_7$ | 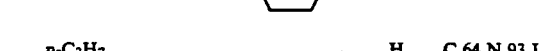 | H | C 64 N 93 I |
| n-$C_3H_7$ | 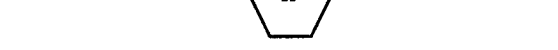 | F | |

-continued

| $C_nH_{2n+1}$-Q-$(CH_2)_r$ | A | L | |
|---|---|---|---|
| n-$C_4H_9$ | cyclohexyl(H) | H | |
| n-$C_4H_9$ | cyclohexyl(H) | F | |
| n-$C_5H_{11}$ | cyclohexyl(H) | H | |
| n-$C_5H_{11}$ | cyclohexyl(H) | F | |
| $CH_3OCH_2$ | cyclohexyl(H) | H | |
| $CH_3OCH_2$ | cyclohexyl(H) | F | |
| $CH_2$=$CHCH_2CH_2$ | cyclohexyl(H) | H | |
| $CH_2$=$CHCH_2CH_2$ | cyclohexyl(H) | F | |
| $C_2H_5$ | phenyl | H | |
| $C_2H_5$ | phenyl | F | |
| n-$C_3H_7$ | phenyl | H | C 72 N (40) I |
| n-$C_3H_7$ | phenyl | F | C 108 I |
| n-$C_4H_9$ | phenyl | H | |
| n-$C_4H_9$ | phenyl | F | |
| n-$C_5H_{11}$ | phenyl | H | C 70 N (59) I |
| n-$C_5H_{11}$ | phenyl | F | C 101 I |
| $CH_3OCH_2$ | phenyl | H | |
| $CH_3OCH_2$ | phenyl | F | |
| $CH_2$=$CHCH_2CH_2$ | phenyl | H | |
| $CH_2$=$CHCH_2CH_2$ | phenyl | F | |

EXAMPLE 3

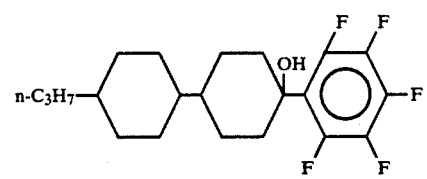

37 ml of a 1.6 molar solution of n-BuLi in hexane are added dropwise at −70° C. to a solution of 50 mmol of pentafluorobenzene in 60 ml of THF. The mixture is stirred for a further hour, then a solution of 50 mmol of 4-(4-n-propylcyclohexyl)cyclohexanone in 40 ml of THF is added dropwise at the same temperature, and 100 ml of 1N hydrochloric acid are added.

The mixture is subsequently subjected to customary work-up, giving, after chromatography, the pentafluorophenylbenzyl alcohol with an axial position of the OH group. C 100 N 110 I.

The following compounds of the formula

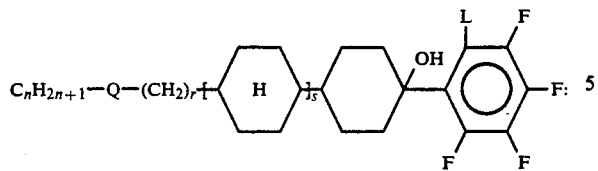

are obtained analogously:

| $C_nH_{2n+1}$—Q—$(CH_2)_r$ | s | L |
|---|---|---|
| $C_2H_5$ | 1 | H |
| $C_2H_5$ | 1 | F |
| n-$C_3H_7$ | 1 | H |
| n-$C_4H_9$ | 1 | H |
| n-$C_4H_9$ | 1 | F |
| n-$C_5H_{11}$ | 1 | H |
| n-$C_5H_{11}$ | 1 | F |
| $CH_3OCH_2$ | 1 | H |
| $CH_3OCH_2$ | 1 | F |
| $CH_3O(CH_2)_3$ | 1 | H |
| $CH_3O(CH_2)_3$ | 1 | F |
| $CH_2$=$CHCH_2CH_2$ | 1 | H |
| $CH_2$=$CHCH_2CH_2$ | 1 | F |
| $C_2H_5$ | 2 | H |
| $C_2H_5$ | 2 | F |
| n-$C_3H_7$ | 2 | H |
| n-$C_3H_7$ | 2 | F |
| n-$C_4H_9$ | 2 | H |
| n-$C_4H_9$ | 2 | F |
| n-$C_5H_{11}$ | 2 | H |
| n-$C_5H_{11}$ | 2 | F |
| $CH_3OCH_2$ | 2 | H |
| $CH_3OCH_2$ | 2 | F |
| $CH_2$=$CHCH_2CH_2$ | 2 | H |

EXAMPLE 4 a)

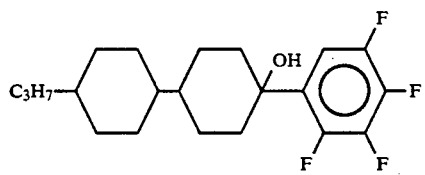

A 1.6 molar solution of n-BuLi in hexane followed by 4-(4-n-propylcyclohexyl)cyclohexanone are added to 50 mmol of 1,2,3,4-tetrafluorobenzene analogously to Example 3.

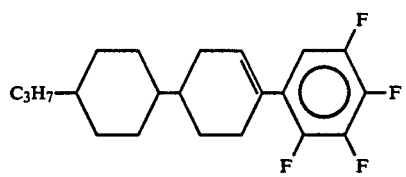

The product from Example 4 a) is dissolved in toluene and refluxed for 5 hours on a water separator with p-toluenesulfonic acid. The mixture is subsequently allowed to cool to room temperature, neutralized and subjected to customary work-up. C 60 N 77 I.

The following compounds of the formula

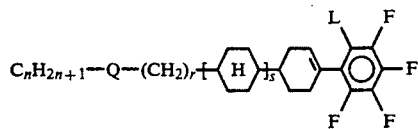

are prepared analogously:

| $C_nH_{2n+1}$—Q—$(CH_2)_r$ | s | L | |
|---|---|---|---|
| $C_2H_5$ | 1 | H | |
| $C_2H_5$ | 1 | F | |
| n-$C_3H_7$ | 1 | F | |
| n-$C_4H_9$ | 1 | H | |
| n-$C_4H_9$ | 1 | F | |
| n-$C_5H_{11}$ | 1 | H | C 46 N 87 I |
| n-$C_5H_{11}$ | 1 | F | |
| $CH_3OCH_2$ | 1 | H | |
| $CH_3OCH_2$ | 1 | F | |
| $CH_3O(CH_2)_3$ | 1 | H | |
| $CH_3O(CH_2)_3$ | 1 | F | |
| $CH_2$=$CHCH_2CH_2$ | 1 | H | |
| $CH_2$=$CHCH_2CH_2$ | 1 | F | |
| $C_2H_5$ | 2 | H | |
| $C_2H_5$ | 2 | F | |
| n-$C_3H_7$ | 2 | H | |
| n-$C_3H_7$ | 2 | F | |
| n-$C_4H_9$ | 2 | H | |
| n-$C_4H_9$ | 2 | F | |
| n-$C_5H_{11}$ | 2 | H | |
| n-$C_5H_{11}$ | 2 | F | |
| $CH_3OCH_2$ | 2 | H | |
| $CH_3OCH_2$ | 2 | H | |
| $CH_3O(CH_2)_3$ | 2 | H | |
| $CH_3O(CH_2)_3$ | 2 | F | |
| $CH_2$=$CHCH_2CH_2$ | 2 | H | |
| $CH_2$=$CHCH_2CH_2$ | 2 | F | |

EXAMPLE 5

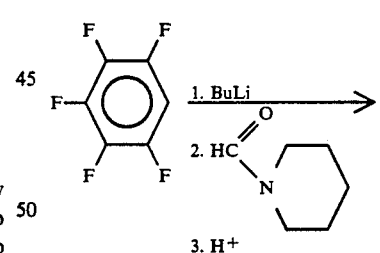

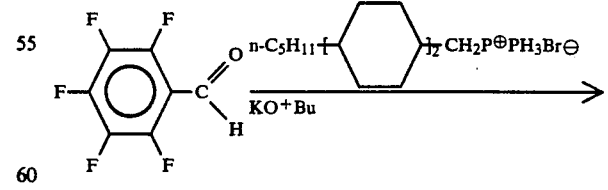

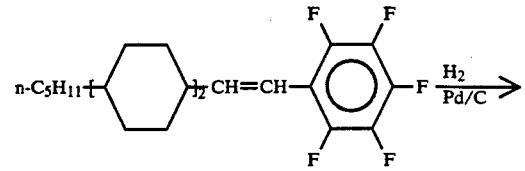

-continued

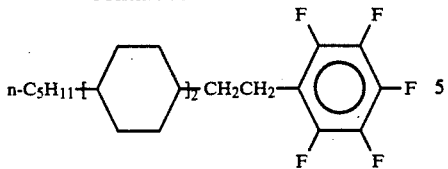

0.1 mol of pentafluorobenzene is metallated at −70° C. in THF using 0.1 mol of BuLi. 0.1 mol of N-formylpiperidine is subsequently added at the same temperature. After hydrolysis, the mixture is subjected to customary work-up and distilled.

0.1 mol of the aldehyde prepared in this way and 0.1 mol of Wittig salt, dissolved in THF, are treated with portions of potassium tert.-butoxide at between 0° and 10° C. The mixture is subsequently stirred at room temperature for 24 hours, poured into water and neutralised and subjected to customary extractive work-up. The alkene produced in recrystallized and hydrogenated in THF using $H_2/Pd/C$ at 1 bar. When the hydrogenation is complete, the solution is concentrated and the residue is purified by recrystallization.

The following compounds of the formula

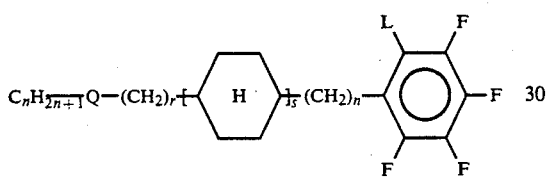

are prepared analogously from the appropriate precursors:

| $C_nH_{2n+1}$—Q—$(CH_2)_r$ | s | n | L |
|---|---|---|---|
| $C_2H_5$ | 1 | 2 | H |
| $C_2H_5$ | 1 | 2 | F |
| $C_2H_5$ | 1 | 4 | H |
| $C_2H_5$ | 1 | 4 | F |
| $C_2H_5$ | 2 | 2 | H |
| $C_2H_5$ | 2 | 2 | F |
| $C_2H_5$ | 2 | 4 | H |
| $C_2H_5$ | 2 | 4 | F |
| n-$C_3H_7$ | 1 | 2 | H |
| n-$C_3H_7$ | 1 | 2 | F |
| n-$C_3H_7$ | 1 | 4 | H |
| n-$C_3H_7$ | 1 | 4 | F |
| n-$C_3H_7$ | 2 | 2 | H |
| n-$C_3H_7$ | 2 | 2 | F |
| n-$C_3H_7$ | 2 | 4 | H |
| n-$C_3H_7$ | 2 | 4 | F |
| n-$C_4H_9$ | 1 | 2 | H |
| n-$C_4H_9$ | 1 | 2 | F |
| n-$C_4H_9$ | 1 | 4 | H |
| n-$C_4H_9$ | 1 | 4 | F |
| n-$C_4H_9$ | 2 | 2 | H |
| n-$C_4H_9$ | 2 | 2 | F |
| n-$C_4H_9$ | 2 | 4 | H |
| n-$C_4H_9$ | 2 | 4 | F |
| n-$C_5H_{11}$ | 1 | 2 | H |
| n-$C_5H_{11}$ | 1 | 4 | H |
| n-$C_5H_{11}$ | 1 | 4 | F |
| n-$C_5H_{11}$ | 2 | 2 | H |
| n-$C_5H_{11}$ | 2 | 2 | F |
| n-$C_5H_{11}$ | 2 | 4 | H |
| n-$C_5H_{11}$ | 2 | 4 | F |
| $CH_3OCH_2$ | 1 | 2 | H |
| $CH_3OCH_2$ | 1 | 2 | F |
| $CH_3OCH_2$ | 1 | 4 | H |
| $CH_3OCH_2$ | 1 | 4 | F |
| $CH_3OCH_2$ | 2 | 2 | H |
| $CH_3OCH_2$ | 2 | 2 | F |
| $CH_3OCH_2$ | 2 | 4 | H |
| $CH_3OCH_2$ | 2 | 4 | F |
| $CH_3O(CH_2)_3$ | 1 | 2 | H |
| $CH_3O(CH_2)_3$ | 1 | 2 | F |
| $CH_3O(CH_2)_3$ | 1 | 4 | H |
| $CH_3O(CH_2)_3$ | 1 | 4 | F |
| $CH_3O(CH_2)_3$ | 2 | 2 | H |
| $CH_3O(CH_2)_3$ | 2 | 2 | F |
| $CH_3O(CH_2)_3$ | 2 | 4 | H |
| $CH_3O(CH_2)_3$ | 2 | 4 | F |
| $CH_2=CHCH_2CH_2$ | 1 | 2 | H |
| $CH_2=CHCH_2CH_2$ | 1 | 2 | F |
| $CH_2=CHCH_2CH_2$ | 1 | 4 | H |
| $CH_2=CHCH_2CH_2$ | 1 | 4 | F |
| $CH_2=CHCH_2CH_2$ | 2 | 2 | H |
| $CH_2=CHCH_2CH_2$ | 2 | 2 | F |
| $CH_2=CHCH_2CH_2$ | 2 | 4 | H |
| $CH_2=CHCH_2CH_2$ | 2 | 4 | F |

EXAMPLE 6

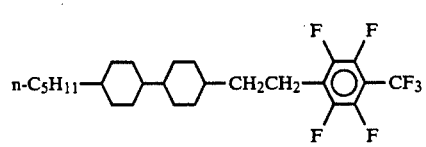

0.1 mol of 1,2,4,5-tetrafluoro-3-trifluoromethylbenzene is metallated analogously to Example 5 at −70° C. in THF using 0.1 mol of BuLi. 0.1 mol of N-formylpiperidine is subsequently added at the same temperature. After hydrolysis and work-up, 0.1 mol of the aldehyde prepared in this way is treated with 0.1 mol of Wittig salt and potassium tert.-butoxide. After the Wittig reaction, the mixture is hydrogenated in THF using $H_2$/Pd-C at 1 bar. The product is finally recrystallized.

The following compounds of the formula

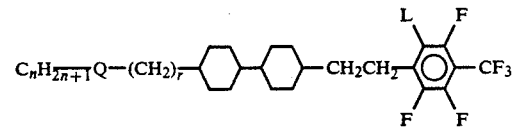

are prepared analogously:

| $C_nH_{2n+1}$—Q—$(CH_2)_r$ | L |
|---|---|
| $C_2H_5$ | H |
| $C_2H_5$ | F |
| n-$C_3H_7$ | H |
| n-$C_3H_7$ | F |
| n-$C_5H_{11}$ | H |
| $CH_3OCH_2$ | H |
| $CH_3OCH_2$ | F |
| $CH_3O(CH_2)_3$ | H |
| $CH_3O(CH_2)_3$ | F |
| $CH_2=CHCH_2CH_2$ | H |
| $CH_2=CHCH_2CH_2$ | F |

EXAMPLE 7

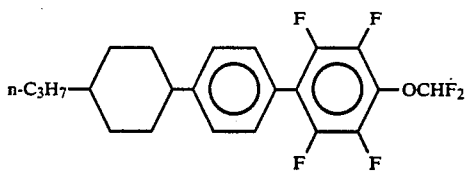

a)

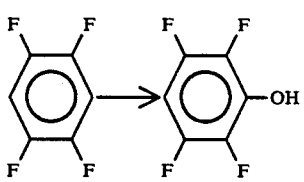

26 mmol of n-BuLi are added dropwise at −100° C. to a mixture comprising 26 mmol of 1,2,4,5-tetrafluorophenol, 4.1 g of potassium tert.-butoxide and 60 ml of THF. After the mixture has been stirred at −100° C. for 1 hour, 36 mmol of trimethyl borate are added dropwise at from −85° and −90° C. The mixture is stirred for a further 0.5 hour, and 42 mmol of acetic acid are then added dropwise at −20° C. The mixture is subsequently warmed to 30° C., 4.2 ml of $H_2O_2$ are added dropwise at this temperature, and the mixture is stirred at from 50° to 60° C. for hours. The mixture is allowed to cool to room temperature, and a 5% sodium dithionate solution is added. Phase separation and customary work-up give the tetrafluorophenol.

b)

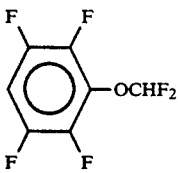

3.1 g of 32% sodium hydroxide solution and 0.5 g of tetrabutylammonium bisulphate are added to 0.01 mol of tetrafluorophenol in THF, the mixture is warmed to 50° C., and chlorodifluoromethane is passed in with stirring until it condenses on a dry ice-cooled condenser. After cooling, the THF solution is subjected to customary work-up.

c)

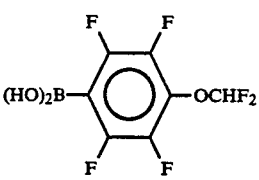

n-BuLi (10.0M in hexane) is added dropwise at −78° under a nitrogen atmosphere to 0.05 mol of 1,2,4,5-tetrafluoro-3-difluoromethoxybenzene in 100 ml of absolute THF. The mixture is stirred for 2.5 hours, triisopropyl borate is added, and the mixture is slowly warmed to room temperature. 10% HCl solution is added, and the mixture is stirred for a further hour. The mixture is subsequently subjected to customary work-up.

d)

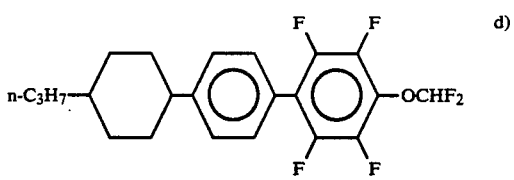

0.05 mol of 4-(4-n-propylcyclohexyl)-1-bromobenzene in ethanol is slowly added dropwise at room temperature under an $N_2$ atmosphere to 40 ml (0.05 mol) of 4-difluoromethoxy-2,3,5,6-tetrafluorophenylboric acid, 1 g of tetrakistriphenylpalladium (0) in 100 ml of benzene and 50 ml of 2N $Na_2CO_3$. The mixture is refluxed, and the reaction is monitored by gas chromatography. When the reaction is complete, the product is extracted with ether and subjected to customary work-up.

The following compounds of the formula

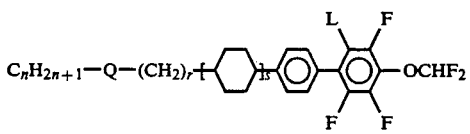

are prepared analogously:

| $C_nH_{2n+1}$—Q—$(CH_2)_r$ | s | L |
| --- | --- | --- |
| $C_2H_5$ | 1 | H |
| $C_2H_5$ | 1 | F |
| $C_2H_5$ | 2 | H |
| $C_2H_5$ | 2 | F |
| n-$C_3H_7$ | 1 | H |
| n-$C_3H_7$ | 2 | H |
| n-$C_3H_7$ | 2 | F |
| n-$C_5H_{11}$ | 1 | H |
| n-$C_5H_{11}$ | 1 | F |
| n-$C_5H_{11}$ | 2 | H |
| n-$C_5H_{11}$ | 2 | F |
| $CH_3OCH_2$ | 1 | H |
| $CH_3OCH_2$ | 1 | F |
| $CH_3OCH_2$ | 2 | H |
| $CH_3OCH_2$ | 2 | F |
| $CH_3O(CH_2)_3$ | 1 | H |
| $CH_3O(CH_2)_3$ | 1 | F |
| $CH_3O(CH_2)_3$ | 2 | H |
| $CH_3O(CH_2)_3$ | 2 | F |
| $CH_2=CHCH_2CH_2$ | 1 | H |
| $CH_2=CHCH_2CH_2$ | 1 | F |
| $CH_2=CHCH_2CH_2$ | 2 | H |
| $CH_2=CHCH_2CH_2$ | 2 | F |

EXAMPLE 8

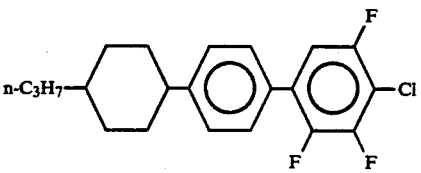

1,2,4-Trifluorobenzene is first metallated using BuLi analogously to Scheme 4. Halogen-metal exchange is then carried out using hexachloroethane. The 1-chloro- 2,3,6-trifluorobenzene is coupled to 4-(4-n-propylcyclohexyl)-1-bromobenzene analogously to Example 7.

The following compounds of the formula

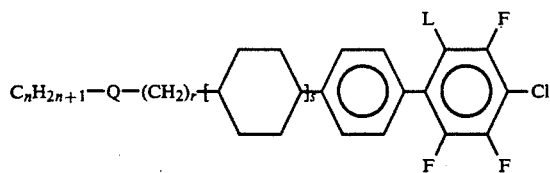

are prepared analogously:

| $C_nH_{2n+1}$—Q—$(CH_2)_r$ | s | L |
|---|---|---|
| $C_2H_5$ | 1 | H |
| $C_2H_5$ | 1 | F |
| $C_2H_5$ | 2 | H |
| $C_2H_5$ | 2 | F |
| n-$C_3H_7$ | 1 | H |
| n-$C_3H_7$ | 2 | H |
| n-$C_3H_7$ | 2 | F |
| n-$C_5H_{11}$ | 1 | H |
| n-$C_5H_{11}$ | 1 | F |
| n-$C_5H_{11}$ | 2 | H |
| n-$C_5H_{11}$ | 2 | F |
| $CH_3OCH_2$ | 1 | H |
| $CH_3OCH_2$ | 1 | F |
| $CH_3OCH_2$ | 2 | H |
| $CH_3OCH_2$ | 2 | F |
| $CH_2=CHCH_2CH_2$ | 1 | H |
| $CH_2=CHCH_2CH_2$ | 1 | F |
| $CH_2=CHCH_2CH_2$ | 2 | H |
| $CH_2=CHCH_2CH_2$ | 2 | F |

EXAMPLE 9

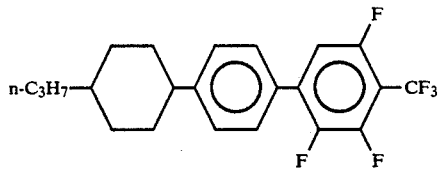

a)

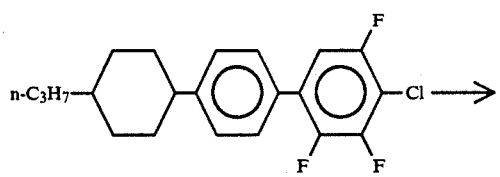

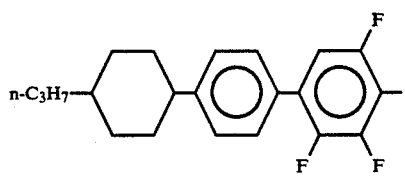

The product obtained from Example 8 is hydrogenated under basic conditions using palladium/activated charcoal to give the trifluorobenzene derivative.

b)

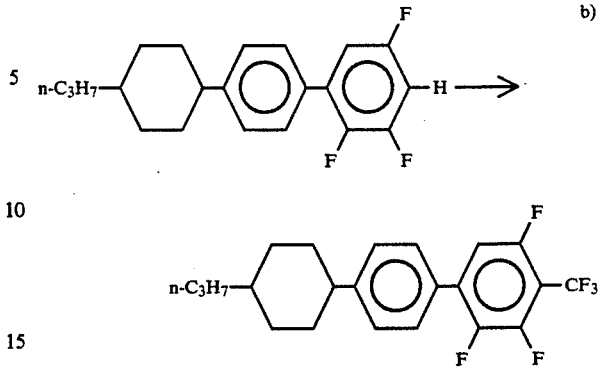

31 ml of n-BuLi (15% in hexane) are added dropwise at from −65° to −70° C. to a mixture of 47 mmol of 4-(4-propylcyclohexyl)-2',3',5'-trifluoromethylbiphenyl, 50 mmol of TMEDA and 150 ml of THF, and the mixture is stirred at −70° C. for a further hour. A solution of 47 mmol of iodine in 25 ml of THF is then added dropwise at from −65° to −70° C., and the mixture is stirred at −70° C. for a further 0.5 hour. The mixture is warmed to −30° C. and hydrolyzed using 15 ml of water, and excess iodine is reduced by adding 15 ml of sodium bisulphite solution. Customary work-up and recrystrallization from hexane gives the trifluoromonoiodobenzene, of which 38 mmol are treated with 76 mmol of KF, 168 mmol of sodium trifluoroacetate and 800 ml of NMP. 400 ml of NMP are removed by distillation at 70° C. and 4 mbar. 76 mmol of dry CuI are then added to the reaction mixture, which is stirred at 160° C. for 5 hours. About 400 ml of NMP are subsequently removed by distillation. The mixture is allowed to cool to room temperature, and 300 ml of methyl tert.-butyl ether are added. The mixture is subsequently subjected to customary work-up.

The following compounds of the formula

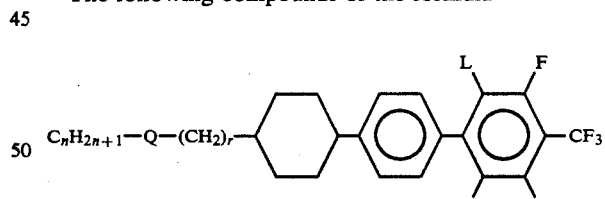

are prepared analogously:

| $C_nH_{2n+1}$—Q—$(CH_2)_r$ | L | |
|---|---|---|
| $C_2H_5$ | H | |
| $C_2H_5$ | F | |
| n-$C_3H_7$ | F | C 96 I |
| n-$C_5H_{11}$ | F | |
| n-$C_5H_{11}$ | H | |
| $CH_3OCH_2$ | H | |
| $CH_3OCH_2$ | F | |
| $CH_2=CHCH_2CH_2$ | H | |
| $CH_2=CHCH_2CH_2$ | F | |

EXAMPLE 10

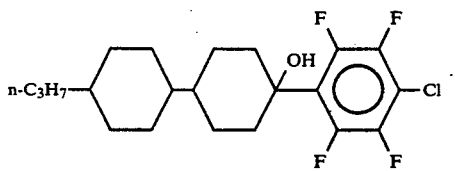

50 mmol of 4-(4-n-propyl-cyclohexyl)cyclohexanone are added, analogously to Example 3, to 50 mmol of 1-chloro-2,3,5,6-tetrafluorobenzene.

The following compounds of the formula

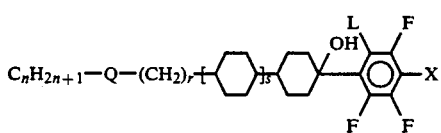

are obtained analogously:

| $C_nH_{2n+1}$—Q—$(CH_2)_r$ | s | L | X |
|---|---|---|---|
| $C_2H_5$ | 1 | H | Cl |
| $C_2H_5$ | 1 | F | Cl |
| $C_2H_5$ | 1 | H | $CF_3$ |
| $C_2H_5$ | 1 | F | $CF_3$ |
| $C_2H_5$ | 1 | H | $OCHF_2$ |
| $C_2H_5$ | 1 | F | $OCHF_2$ |
| $C_2H_5$ | 2 | H | Cl |
| $C_2H_5$ | 2 | F | Cl |
| $C_2H_5$ | 2 | H | $CF_3$ |
| $C_2H_5$ | 2 | F | $CF_3$ |
| $C_2H_5$ | 2 | H | $OCHF_2$ |
| $C_2H_5$ | 2 | F | $OCHF_2$ |
| n-$C_3H_7$ | 1 | H | Cl |
| n-$C_3H_7$ | 1 | F | Cl |
| n-$C_3H_7$ | 1 | H | $CF_3$ |
| n-$C_3H_7$ | 1 | F | $CF_3$ |
| n-$C_3H_7$ | 1 | H | $OCHF_2$ |
| n-$C_3H_7$ | 1 | F | $OCHF_2$ |
| n-$C_3H_7$ | 2 | H | Cl |
| n-$C_3H_7$ | 2 | F | Cl |
| n-$C_3H_7$ | 2 | H | $CF_3$ |
| n-$C_3H_7$ | 2 | F | $CF_3$ |
| n-$C_3H_7$ | 2 | H | $OCHF_2$ |
| n-$C_3H_7$ | 2 | F | $OCHF_2$ |
| n-$C_2H_{11}$ | 1 | H | Cl |
| n-$C_2H_{11}$ | 1 | F | Cl |
| n-$C_2H_{11}$ | 1 | H | $CF_3$ |
| n-$C_2H_{11}$ | 1 | F | $CF_3$ |
| n-$C_2H_{11}$ | 1 | H | $OCHF_2$ |
| n-$C_2H_{11}$ | 1 | F | $OCHF_2$ |
| n-$C_2H_{11}$ | 2 | H | Cl |
| n-$C_2H_{11}$ | 2 | F | Cl |
| n-$C_2H_{11}$ | 2 | H | $CF_3$ |
| n-$C_2H_{11}$ | 2 | F | $CF_3$ |
| n-$C_2H_{11}$ | 2 | H | $OCHF_2$ |
| n-$C_2H_{11}$ | 2 | F | $OCHF_2$ |
| $CH_2OCH_2$ | 1 | H | Cl |
| $CH_2OCH_2$ | 1 | F | Cl |
| $CH_2OCH_2$ | 1 | H | $CF_3$ |
| $CH_2OCH_2$ | 1 | F | $CF_3$ |
| $CH_2OCH_2$ | 1 | H | $OCHF_2$ |
| $CH_2OCH_2$ | 1 | F | $OCHF_2$ |
| $CH_2OCH_2$ | 2 | H | Cl |
| $CH_2OCH_2$ | 2 | F | Cl |
| $CH_2OCH_2$ | 2 | H | $CF_3$ |
| $CH_2OCH_2$ | 2 | F | $CF_3$ |
| $CH_2OCH_2$ | 2 | H | $OCHF_2$ |
| $CH_2OCH_2$ | 2 | F | $OCHF_2$ |
| $CH_3O(CH_2)_3$ | 1 | H | Cl |
| $CH_3O(CH_2)_3$ | 1 | F | Cl |
| $CH_3O(CH_2)_3$ | 1 | H | $CF_3$ |
| $CH_3O(CH_2)_3$ | 1 | F | $CF_3$ |
| $CH_3O(CH_2)_3$ | 1 | H | $OCHF_2$ |
| $CH_3O(CH_2)_3$ | 1 | F | $OCHF_2$ |
| $CH_3O(CH_2)_3$ | 2 | H | Cl |
| $CH_3O(CH_2)_3$ | 2 | F | Cl |
| $CH_3O(CH_2)_3$ | 2 | H | $CF_3$ |
| $CH_3O(CH_2)_3$ | 2 | F | $CF_3$ |
| $CH_3O(CH_2)_3$ | 2 | H | $OCHF_2$ |
| $CH_3O(CH_2)_3$ | 2 | F | $OCHF_2$ |
| $CH_2$=$CH_2CH_2$ | 1 | H | Cl |
| $CH_2$=$CH_2CH_2$ | 1 | F | Cl |
| $CH_2$=$CH_2CH_2$ | 1 | H | $CF_3$ |
| $CH_2$=$CH_2CH_2$ | 1 | F | $CF_3$ |
| $CH_2$=$CH_2CH_2$ | 1 | H | $OCHF_2$ |
| $CH_2$=$CH_2CH_2$ | 1 | F | $OCHF_2$ |
| $CH_2$=$CH_2CH_2$ | 2 | H | Cl |
| $CH_2$=$CH_2CH_2$ | 2 | F | Cl |
| $CH_2$=$CH_2CH_2$ | 2 | H | $CF_3$ |
| $CH_2$=$CH_2CH_2$ | 2 | F | $CF_3$ |
| $CH_2$=$CH_2CH_2$ | 2 | H | $OCHF_2$ |
| $CH_2$=$CH_2CH_2$ | 2 | F | $OCHF_2$ |

EXAMPLE 11

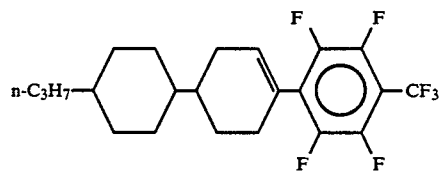

The product from Example 10 is dissolved in toluene and refluxed for 5 hours with p-toluenesulfonic acid. The mixture is subsequently allowed to cool to room temperature, neutralized and subjected to customary work-up.

The following compounds of the formula

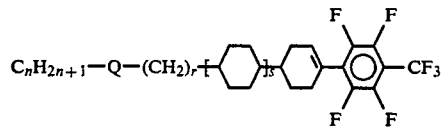

are prepared analogously:

| $C_nH_{2n+1}$—Q—$(CH_2)_r$ | s | L | X |
|---|---|---|---|
| $C_2H_5$ | 1 | H | Cl |
| $C_2H_5$ | 1 | F | Cl |
| $C_2H_5$ | 1 | H | $CF_3$ |
| $C_2H_5$ | 1 | F | $CF_3$ |
| $C_2H_5$ | 1 | H | $OCHF_2$ |
| $C_2H_5$ | 1 | F | $OCHF_2$ |
| $C_2H_5$ | 2 | H | Cl |
| $C_2H_5$ | 2 | F | Cl |
| $C_2H_5$ | 2 | H | $CF_3$ |
| $C_2H_5$ | 2 | F | $CF_3$ |
| $C_2H_5$ | 2 | H | $OCHF_2$ |
| n-$C_3H_7$ | 2 | F | $OCHF_2$ |
| n-$C_3H_7$ | 1 | H | Cl |
| n-$C_3H_7$ | 1 | F | Cl |
| n-$C_3H_7$ | 1 | H | $CF_3$ |
| n-$C_3H_7$ | 1 | F | $CF_3$ |
| n-$C_3H_7$ | 1 | H | $OCHF_2$ |
| n-$C_3H_7$ | 1 | F | $OCHF_2$ |
| n-$C_3H_7$ | 2 | H | Cl |
| n-$C_3H_7$ | 2 | F | Cl |
| n-$C_3H_7$ | 2 | H | $CF_3$ |
| n-$C_3H_7$ | 2 | F | $CF_3$ |
| n-$C_3H_7$ | 2 | H | $OCHF_2$ |
| n-$C_3H_7$ | 2 | F | $OCHF_2$ |
| n-$C_2H_{11}$ | 1 | H | Cl |
| n-$C_2H_{11}$ | 1 | F | Cl |

-continued

| $C_nH_{2n+1}$—Q—$(CH_2)_r$ | s | L | X |
|---|---|---|---|
| n-$C_2H_{11}$ | 1 | H | $CF_3$ |
| n-$C_2H_{11}$ | 1 | F | $CF_3$ |
| n-$C_2H_{11}$ | 1 | H | $OCHF_2$ |
| n-$C_2H_{11}$ | 1 | F | $OCHF_2$ |
| n-$C_2H_{11}$ | 2 | H | Cl |
| n-$C_2H_{11}$ | 2 | F | Cl |
| n-$C_2H_{11}$ | 2 | H | $CF_3$ |
| n-$C_2H_{11}$ | 2 | F | $CF_3$ |
| n-$C_2H_{11}$ | 2 | H | $OCHF_2$ |
| n-$C_2H_{11}$ | 2 | F | $OCHF_2$ |
| $CH_2OCH_2$ | 1 | H | Cl |
| $CH_2OCH_2$ | 1 | F | Cl |
| $CH_2OCH_2$ | 1 | H | $CF_3$ |
| $CH_2OCH_2$ | 1 | F | $CF_3$ |
| $CH_2OCH_2$ | 1 | H | $OCHF_2$ |
| $CH_2OCH_2$ | 1 | F | $OCHF_2$ |
| $CH_2OCH_2$ | 2 | H | Cl |
| $CH_2OCH_2$ | 2 | F | Cl |
| $CH_2OCH_2$ | 2 | H | $CF_3$ |
| $CH_2OCH_2$ | 2 | F | $CF_3$ |
| $CH_2OCH_2$ | 2 | H | $OCHF_2$ |
| $CH_2OCH_2$ | 2 | F | $OCHF_2$ |
| $CH_3O(CH_2)_3$ | 1 | H | Cl |
| $CH_3O(CH_2)_3$ | 1 | F | Cl |
| $CH_3O(CH_2)_3$ | 1 | H | $CF_3$ |
| $CH_3O(CH_2)_3$ | 1 | F | $CF_3$ |
| $CH_3O(CH_2)_3$ | 1 | H | $OCHF_2$ |
| $CH_3O(CH_2)_3$ | 1 | F | $OCHF_2$ |
| $CH_3O(CH_2)_3$ | 2 | H | Cl |
| $CH_3O(CH_2)_3$ | 2 | F | Cl |
| $CH_3O(CH_2)_3$ | 2 | H | $CF_3$ |
| $CH_3O(CH_2)_3$ | 2 | F | $CF_3$ |
| $CH_3O(CH_2)_3$ | 2 | H | $OCHF_2$ |
| $CH_3O(CH_2)_3$ | 2 | F | $OCHF_2$ |
| $CH_2=CH_2CH_2$ | 1 | H | Cl |
| $CH_2=CH_2CH_2$ | 1 | F | Cl |
| $CH_2=CH_2CH_2$ | 1 | H | $CF_3$ |
| $CH_2=CH_2CH_2$ | 1 | F | $CF_3$ |
| $CH_2=CH_2CH_2$ | 1 | H | $OCHF_2$ |
| $CH_2=CH_2CH_2$ | 1 | F | $OCHF_2$ |
| $CH_2=CH_2CH_2$ | 2 | H | Cl |
| $CH_2=CH_2CH_2$ | 2 | F | Cl |
| $CH_2=CH_2CH_2$ | 2 | H | $CF_3$ |
| $CH_2=CH_2CH_2$ | 2 | F | $CF_3$ |
| $CH_2=CH_2CH_2$ | 2 | H | $OCHF_2$ |
| $CH_2=CH_2CH_2$ | 2 | F | $OCHF_2$ |

EXAMPLE 12

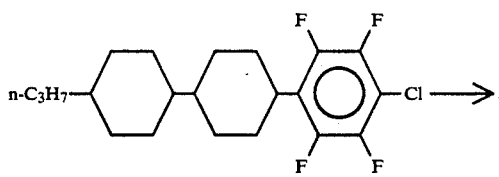

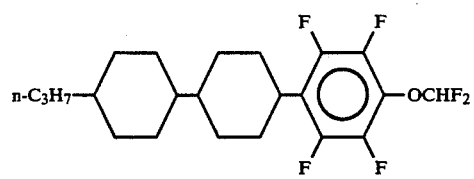

The product from Example 11 is first hydrogenated under acidic conditions using Raney nickel. This is followed by hydrogenation under basic conditions on a Pd/C catalyst. The tetrafluorobenzene derivative obtained is then converted into the difluoromethoxytetrafluorobenzene derivative as in Example 7.

The following compounds of the formula

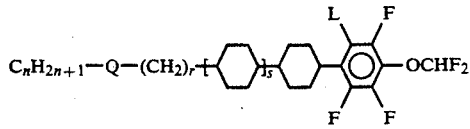

are prepared analogously:

| $C_nH_{2n+1}$—Q—$(CH_2)_r$ | s | L |
|---|---|---|
| $C_2H_5$ | 1 | H |
| $C_2H_5$ | 1 | F |
| $C_2H_5$ | 2 | H |
| $C_2H_5$ | 2 | F |
| n-$C_3H_7$ | 1 | H |
| n-$C_3H_7$ | 1 | H |
| n-$C_3H_7$ | 1 | F |
| n-$C_2H_{11}$ | 1 | H |
| n-$C_2H_{11}$ | 1 | F |
| n-$C_2H_{11}$ | 1 | H |
| n-$C_2H_{11}$ | 2 | H |
| n-$C_2H_{11}$ | 2 | F |
| $CH_2OCH_2$ | 1 | H |
| $CH_2OCH_2$ | 1 | F |
| $CH_2OCH_2$ | 2 | H |
| $CH_2OCH_2$ | 2 | F |
| $CH_3O(CH_2)_3$ | 1 | H |
| $CH_3O(CH_2)_3$ | 1 | F |
| $CH_3O(CH_2)_3$ | 2 | H |
| $CH_3O(CH_2)_3$ | 2 | F |
| $CH_2=CH_2CH_2$ | 1 | H |
| $CH_2=CH_2CH_2$ | 1 | F |
| $CH_2=CH_2CH_2$ | 2 | H |
| $CH_2=CH_2CH_2$ | 2 | F |

The examples below relate to liquid-crystalline media:

EXAMPLE A

| | | |
|---|---|---|
| PCH-5F | 9.0% | $T_c$ = 75° C. |
| PCH-6F | 7.2% | $\Delta n$ = 0,0887 |
| PCH-7F | 5.4% | $\Delta\epsilon$ = 4,82 |
| CCP-20$CF_3$ | 7.2% | |
| CCP-30$CF_3$ | 10.8% | |
| CCP-40$CF_3$ | 6.3% | |
| CCP-50$CF_3$ | 9.9% | |
| BCH-3F.F | 10.8% | |
| BCH-5F.F | 9.0% | |
| ECCP-30$CF_3$ | 4.5% | |
| ECCP-50$CF_3$ | 4.5% | |
| CBC-33F | 1.8% | |
| CBC-53F | 1.8% | |
| CBC-55F | 1.8% | |
| CCP-3F[4] | 10.0% | |

EXAMPLE B

| | | |
|---|---|---|
| PCH-5F | 5.0% | $T_c$ = 88° C. |
| PCH-7F | 6.0% | $\Delta n$ = 0,094 |
| CCP-20$CF_3$ | 11.0% | $V_{(10,0,20)}$ = 1,58 V |
| CCP-30$CF_3$ | 12.0% | $V_{(50,0,20)}$ = 2,03 V |
| CCP-40$CF_3$ | 10.0% | $V_{(90,0,20)}$ = 2,62 V |
| CCP-50$CF_3$ | 12.0% | |
| BCH-3F.F.F | 12.0% | |
| BCH-5F.F.F | 11.0% | |
| CCP-5F.F.F | 9.0% | |
| CCP-3F[4] | 12.0% | |

EXAMPLE C

| | | |
|---|---|---|
| PCH-5F | 5.0% | $T_c$ = 87° C. |

-continued

| | | |
|---|---|---|
| PCH-7F | 6.0% | Δn = 0,094 |
| CCP-20CF₃ | 11.0% | V₍₁₀,₀,₂₀₎ = 1,62 V |
| CCP-30CF₃ | 12.0% | V₍₅₀,₀,₂₀₎ = 2,06 V |
| CCP-40CF₃ | 10.0% | V₍₉₀,₀,₂₀₎ = 2,67 V |
| CCP-50CF₃ | 12.0% | |
| BCH-3F.F.F | 12.0% | |
| BCH-5F.F.F | 11.0% | |
| CCP-3F⁴ | 21.0% | |

EXAMPLE D

| | | |
|---|---|---|
| PCH-5F | 5.0% | $T_c$ = 109° C. |
| PCH-7F | 6.0% | Δn = 0,0839 |
| CCP-20CF₃ | 11.0% | $V_{(10,0,20)}$ = 2,17 V |
| CCP-30CF₃ | 12.0% | $V_{(50,0,20)}$ = 2,68 V |
| CCP-40CF₃ | 10.0% | $V_{(90,0,20)}$ = 3,45 V |
| CCP-50CF₃ | 12.0% | |
| CCP-30CF₃ | 12.0% | |
| CCP-50CF₃ | 11.0% | |
| CCP-3F⁴ | 21.0% | |

EXAMPLE E

| | | |
|---|---|---|
| PCH-5F | 5.0% | $T_c$ = 88° C. |
| PCH-7F | 6.0% | Δn = 0,0914 |
| CCP-20CF₃ | 11.0% | $V_{(10,0,20)}$ = 1,73 V |
| CCP-30CF₃ | 12.0% | $V_{(50,0,20)}$ = 2,10 V |
| CCP-40CF₃ | 10.0% | $V_{(90,0,20)}$ = 2,61 V |
| CCP-50CF₃ | 12.0% | |
| CUP-30CF₃ | 12.0% | |
| CUP-50CF₃ | 11.0% | |
| CCP-3F⁴ | 21.0% | |

EXAMPLE F

| | | |
|---|---|---|
| PCH-5F | 8.0% | $T_c$ = 89° C. |
| PCH-6F | 6.4% | ΔN = +0,0933 |
| PCH-7F | 4.8% | Δε = +5,5 |
| CCP-20CF₃ | 6.4% | $V_{(10,0,20)}$ = 1,88 V |
| CCP-30CF₃ | 9.6% | $V_{(50,0,20)}$ = 2,33 V |
| CCP-40CF₃ | 5.6% | $V_{(90,0,20)}$ = 2,96 V |
| CCP-50CF₃ | 8.8% | |
| BCH-3F.F | 9.6% | |
| BCH-5F.F | 8.0% | |
| ECCP-30CF₃ | 4.0% | |
| ECCP-50CF₃ | 4.0% | |
| CBC-33F | 1.6% | |
| CBC-53F | 1.6% | |
| CBC-55F | 1.6% | |
| CBC-3F⁴ | 20.0% | |

EXAMPLE G

| | | |
|---|---|---|
| PCH-5F | 8.0% | S → N + 49° C. |
| PCH-6F | 6.4% | |
| PCH-7F | 4.8% | |
| CCP-20CF₃ | 6.4% | |
| CCP-30CF₃ | 9.6% | |
| CCP-40CF₃ | 5.6% | |
| CCP-50CF₃ | 8.8% | |
| BCH-3F.F | 9.6% | |
| BCH-5F.F | 8.0% | |
| ECCP-30CF₃ | 4.0% | |
| ECCP-50CF₃ | 4.0% | |
| CBC-33F | 1.6% | |
| CBC-53F | 1.6% | |
| CBC-55F | 1.6% | |
| CCP-3F⁴ | 20.0% | |

EXAMPLE H

| | | |
|---|---|---|
| PCH-5F | 9.0% | Δn = +0,0992 |
| PCH-6F | 7.2% | Δε = +5,2 |
| PCH-7F | 5.4% | $V_{(10,0,20)}$ = 2,03 V |
| CCP-20CF₃ | 7.2% | $V_{(50,0,20)}$ = 2,48 V |
| CCP-30CF₃ | 10.8% | $V_{(90,0,20)}$ = 3,18 V |
| CCP-40CF₃ | 6.3% | |
| CCP-50CF₃ | 9.9% | |
| BCH-3F.F | 10.8% | |
| BCH-5F.F | 9.0% | |
| ECCP-30CF₃ | 4.5% | |
| ECCP-50CF₃ | 4.5% | |
| CBC-33F | 1.8% | |
| CBC-53F | 1.8% | |
| CBC-55F | 1.8% | |
| CCP-3F⁴ | 10.0% | |

We claim:

1. A benzene compound of formula I

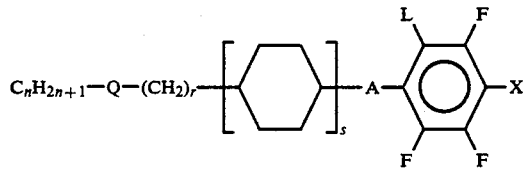

wherein
n is 0, 1, 2, 3, 4, 5, 6 or 7;
Q is —O—, —CH=CH— or a single bond;
r is 0, 1, 2, 3, 4, or 5;
s is 0, 1 or 2, s being 1 or 2 if A is a single bond;
X is F, Cl, OCHF₂ or CF₃;
L is H; and
A is Z, Z-Ar, Ar-Z, or Z-Cyc;
Z is a single bond, —(CH₂)₂— or —(CH₂)₄—;
Ar is 1,4-phenylene or biphenyl-4,4'-diyl; and
Cyc is trans-1,4-cyclohexylene.

2. A compound according to claim 1, wherein said compound is of formula Ia,

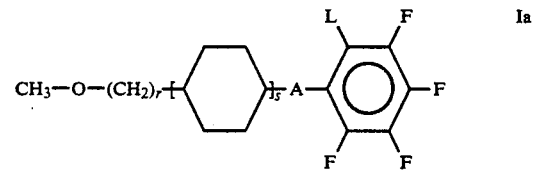

wherein
r is 2, 3, 4 or 5;
s is 1 or 2;
A is Z, Z-Ar, Ar-Z, or Z-Cyc; and
L is H.

3. A compound according to claim 1, wherein said compound is of formula Ib

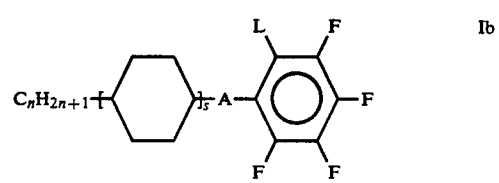

wherein
n is 1 to 7;

s is 1 or 2;
L is H; and
A is Z, Z-Ar, Ar-Z, or Z-Cyc.

4. A compound according to claim 3, wherein s is 2 and A is Z.

5. A compound according to claim 3, wherein s is 1 and A is Ar.

6. A compound according to claim 4, wherein Z is a single bond.

7. A compound according to claim 4, wherein Z is —(CH$_2$)$_2$—.

8. A compound according to claim 1, wherein said compound is of formula Ie

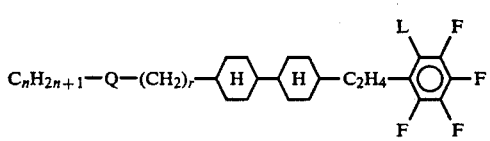

wherein
n is 1 to 7;
Q is —O—, —CH=CH— or a single bond;
r is 0, 1, 2, 3, 4 or 5; and
L is H.

9. A compound according to claim 1, wherein said compound is of formula If

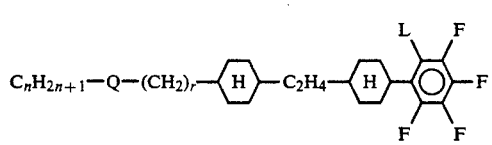

wherein
n is 1 to 7;
Q is —O—, —CH=CH— or a single bond;
r is 0, 1, 2, 3, 4 or 5; and
L is H.

10. In a liquid-crystalline medium for electrooptical displays having at least two liquid-crystalline components, the improvement comprising at least one component is a compound according to claim 1.

11. In an electrooptical display device containing a liquid-crystal cell, the improvement comprising said liquid-crystal cell containing a medium according to claim 10.

12. In a method of generating an optical display using an electrooptical display device, the improvement wherein said electrooptical display device is a device according to claim 11.

13. A compound according to formula Ic

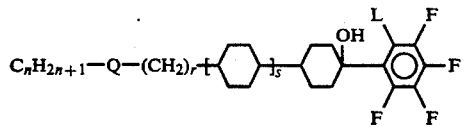

wherein
n is 1 to 7;
s is 0, 1 or 2;
Q is —O—, —CH=CH— or a single bond;

r is 0, 1, 2, 3, 4 or 5; and
L is H.

14. A compound wherein said compound is of formula Ia,

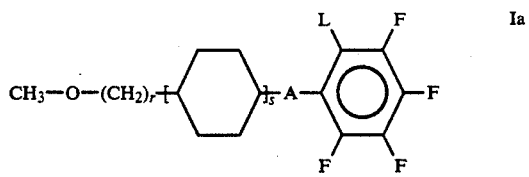

wherein
r is 2, 3, 4 or 5;
s is 1 or 2;
A is Z, Z-Ar, Ar-Z, or Z-Cyc;
L is H or F;
Z is a single bond, —(CH$_2$)$_2$— or —(CH$_2$)$_4$—;
Ar is 1,4-phenylene or biphenyl-4,4'-diyl; and
Cyc is trans-1,4-cyclohexylene.

15. A compound of formula Ib,

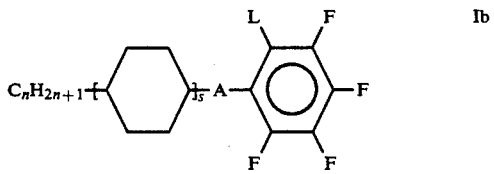

wherein
n is 1 to 7;
L is H or F;
s is 1; and
A is 1,4-phenylene or biphenyl-4,4'-diyl.

16. A compound of formula Ib,

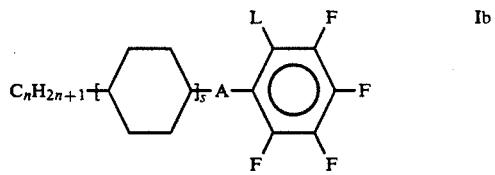

wherein
n is 1 to 7;
s is 2;
A is —(CH$_2$)$_2$—; and
L is H or F.

17. A compound of formula Ic

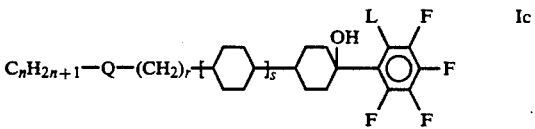

wherein
n is 1 to 7;
s is 0, 1 or 2;
Q is —O—, —CH=CH— or a single bond;
r is 0, 1, 2, 3, 4 or 5; and
L is H or F.

* * * * *